(12) United States Patent
Popoola et al.

(10) Patent No.: US 7,833,274 B2
(45) Date of Patent: Nov. 16, 2010

(54) KNEE SYSTEM AND METHOD OF MAKING SAME

(75) Inventors: Oludele O. Popoola, Granger, IN (US); Joel G. Scrafton, Leesburg, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 12/353,692

(22) Filed: Jan. 14, 2009

(65) Prior Publication Data

US 2009/0125115 A1 May 14, 2009

Related U.S. Application Data

(63) Continuation-in-part of application No. 11/749,598, filed on May 16, 2007, now abandoned.

(60) Provisional application No. 61/020,900, filed on Jan. 14, 2008.

(51) Int. Cl.
*A61F 2/38* (2006.01)

(52) U.S. Cl. .............. 623/20.35; 623/20.18; 623/20.14

(58) Field of Classification Search .............. 623/20.18, 623/20.35
See application file for complete search history.

(56) References Cited

U.S. PATENT DOCUMENTS

| | | | |
|---|---|---|---|
| 4,034,418 A | 7/1977 | Jackson et al. | |
| 4,207,627 A | 6/1980 | Cloutier | |
| 4,257,128 A | 3/1981 | Scales et al. | |
| 4,355,429 A | 10/1982 | Mittelmeier et al. | |
| 5,021,061 A | 6/1991 | Wevers et al. | |
| 5,037,438 A | 8/1991 | Davidson | |
| 5,171,282 A | 12/1992 | Pequignot | |
| 5,180,394 A | 1/1993 | Davidson | |
| 5,282,868 A | 2/1994 | Bahler | |
| 5,358,529 A | 10/1994 | Davidson | |
| 6,045,581 A | 4/2000 | Burkinshaw | |
| 6,105,235 A | 8/2000 | Caldarise | |
| 6,203,844 B1 | 3/2001 | Park | |

(Continued)

FOREIGN PATENT DOCUMENTS

DE 10051437 A1 4/2002

(Continued)

OTHER PUBLICATIONS

Bionic surface design in metal on metal bearings for total hip arthroplasty—Optimization of tribological characteristics, U. Bohling et al., Biomed Technik 50 (2005) 119-123 (BIONIC).

(Continued)

*Primary Examiner*—Bruce E Snow
*Assistant Examiner*—Melissa Montano
(74) *Attorney, Agent, or Firm*—Baker & Daniels LLP (57) ABSTRACT

A femoral prosthesis may be formed as a femoral component incorporating a base material and an articulating material. In one exemplary embodiment, the base material is a metal and the articulating material is a polymer. Specifically, the base material provides strength and rigidity to the femoral component, while the articulating material contacts a tibial prosthesis or natural tibia during joint articulation. In one exemplary embodiment, the articulating material forms the articulating surface of one or more condyle portions of the femoral component.

7 Claims, 5 Drawing Sheets

U.S. PATENT DOCUMENTS

| | | |
|---|---|---|
| 6,214,051 B1 | 4/2001 | Badorf et al. |
| 6,383,222 B1 | 5/2002 | Badorf |
| 6,447,550 B1 | 9/2002 | Hunter et al. |
| 6,652,586 B2 | 11/2003 | Hunter et al. |
| 6,660,040 B2 | 12/2003 | Chan et al. |
| 6,726,725 B2 | 4/2004 | Hunter et al. |
| 2002/0187251 A1 | 12/2002 | Badorf et al. |
| 2003/0208280 A1 | 11/2003 | Tohidi |
| 2006/0052875 A1 | 3/2006 | Bernero et al. |
| 2007/0032877 A1 | 2/2007 | Whiteside |
| 2007/0118227 A1 | 5/2007 | King et al. |
| 2007/0233266 A1 | 10/2007 | Williams, III et al. |
| 2008/0288081 A1 | 11/2008 | Scrafton et al. |

FOREIGN PATENT DOCUMENTS

| | | |
|---|---|---|
| DE | 202006012902 U1 | 10/2006 |
| EP | 0519872 A1 | 12/1992 |
| EP | 1992309 A1 | 11/2008 |
| WO | WO03049781 A1 | 6/2003 |
| WO | WO2007090784 A1 | 8/2007 |
| WO | WO2007109714 A2 | 9/2007 |

OTHER PUBLICATIONS

Office Action mailed Jan. 8, 2009 in U.S. Appl. No. 11/749,598.

The International Search Report and Written Opinion mailed Nov. 17, 2009 in related International Application No. PCT/US2009/030956.

FIG_1

FIG_2

FIG_3

FIG_4

FIG_7

FIG_11

FIG_8

FIG_9

FIG_10

KNEE SYSTEM AND METHOD OF MAKING SAME

CROSS-REFERENCE TO RELATED APPLICATIONS

This application claims the benefit under Title 35 U.S.C. §119(e) of U.S. Provisional Patent Application Ser. No. 61/020,900, entitled A KNEE SYSTEM AND METHOD OF MAKING SAME, filed on Jan. 14, 2008, and under Title 35 U.S.C. §120 of U.S. patent application Ser. No. 11/749,598, entitled IMPLANT ARTICULAR SURFACE WEAR REDUCTION SYSTEM, filed May 16, 2007, the entire disclosures of which are expressly incorporated by reference herein.

BACKGROUND

1. Field of the Invention

The present invention relates to knee prostheses and, particularly, to femoral and tibial prostheses.

2. Description of the Related Art

Prostheses are commonly utilized to repair and/or replace damaged bone and tissue in the human body. For example, a knee prosthesis may be implanted to replace damaged or destroyed bone in the tibia and/or femur and to recreate the natural, anatomical articulation of the knee joint. In a femoral prosthesis, the prosthesis may be shaped to replicate one or both of the natural femoral condyles. A femoral prosthesis may be formed entirely of a rigid metal, which can be formed in complicated geometries and withstand the unique load patterns experienced by the femoral component. After resecting the distal end of the femur, one side of the femoral component is secured to the bone stock of the femur and the opposing side of the femoral component is configured for articulation against a prosthetic tibial component or the natural tibia.

A prosthetic tibial component may include a first, articulating component having a concave condyle portion configured for articulation against the femoral component. The articulating component of the tibial prosthesis may be secured to a tray component that has an opposing side for securing the tibial prosthesis to the bone stock of a resected proximal tibia. The articulating component of the tibial prosthesis may be made from a polymer to facilitate articulation with the femoral component, while the tray component of the tibial prosthesis may be made from a metal to provide additional strength and rigidity to the tibial prosthesis. In this manner, the femoral component and tibial component work together to replicate the natural, anatomical articulation of the knee joint.

SUMMARY

The present invention relates to knee prostheses and, particularly, to femoral and tibial prostheses. In one exemplary embodiment, a femoral prosthesis is formed as a femoral component incorporating a base material and an articulating material. In one exemplary embodiment, the base material is a metal and the articulating material is a polymer. The base material provides strength and rigidity to the femoral component, while the articulating material contacts a tibial prosthesis or natural tibia during joint articulation. In one exemplary embodiment, the articulating material forms the articulating surface of one or more condyle portions of the femoral component. Additionally, by utilizing a base material, such as a metal, that is sufficiently rigid, the base material provides support and rigidity to the articulating material. In one exemplary embodiment, the base material surrounds the articulating material to provide additional support and rigidity to the sides of the articulating material. By utilizing a femoral component having a rigid base material that substantially surrounds a more resilient articulating material defining an articulating surface, stress at the edges of the articular surface that are generated during knee articulation are absorbed by the base material. As a result, delamination of, i.e., the peeling off of, the articulating material is substantially prevented.

In another exemplary embodiment, a tibial prosthesis is provided in the form of a tibial component including an articulating surface and an attachment surface. The attachment surface of the tibial component is configured for attachment to the resected proximal end of a tibia and the articulating surface is configured for articulating against the condyle portion of a femoral component and/or of the natural femur. In one exemplary embodiment, the articulating surface and the attachment surface of the tibial component are formed from a single material. For example, the entire tibial component may be formed from a metal or a ceramic.

By forming the tibial component from a single material, the strength and rigidity of the tibial component is maintained throughout its entirety. Additionally, any potential backside wear of the tibial component, i.e., wear between an articulating component and a tray component, is eliminated. In another exemplary embodiment, the tibial component may be formed from a plurality of materials. In this embodiment, the articulating surface may be formed from a metal and/or ceramic, while the attachment surface of the tibial component may be formed from a polymer. In one exemplary embodiment, the attachment surface may be secured directly to the resected proximal tibia. Alternatively, in another exemplary embodiment, the tibial component may be seated upon a tibial tray component that provides additional rigidity to the tibial component and cooperates with the tibial component to form the tibial prosthesis. Additionally, by providing a polymer layer between the resected proximal tibial or the tray component and the articulating surface, a cushioning effect may be provided within the knee prosthesis, which may provide a better fit and feel to the patient.

Advantageously, by forming the articulating surface of the femoral component from a polymer and forming the articulating surface of the tibial component from a metal and/or a ceramic, the wear of a prosthetic knee incorporating the femoral and tibial prostheses of the present invention is substantially reduced. For example, preliminary testing has indicated that the present design results in a reduction in wear of up to 35% over traditional knee prosthesis designs in which the femoral component is metal or ceramic and the articulating surface of the tibial component is a polymer.

In one form thereof, the present invention provides a knee prosthesis, including: a femoral component formed from a non-polymeric base material and a polymer articulating material, the femoral component having at least one condyle portion formed from the non-polymeric base material, the at least one condyle portion having an upper surface and a wall at least partially defining a groove, the polymer articulating material received within the groove, the wall of the at least one condyle portion surrounding the polymer articulating material, the polymer articulating material defining an articulation surface configured for articulation against one of a tibial prosthesis and a resected proximal tibia, the articulation surface of the polymer articulating material positioned substantially flush with the upper surface of the at least one condyle portion.

In another form thereof, the present invention provides a tibial prosthesis, including: a tibial component having a polymeric body and at least one non-polymeric articulating portion, the polymeric body having an upper surface, the at least one non-polymeric articulating portion having a perimeter and an articulating surface configured for articulating with one of a femoral prosthesis and a natural femur, the non-polymeric articulating portion received within the polymeric body, wherein the polymeric body surrounds the perimeter of the non-polymeric articulating portion and the articulating surface of the non-polymeric articulating portion is substantially flush with the upper surface of the polymeric body.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
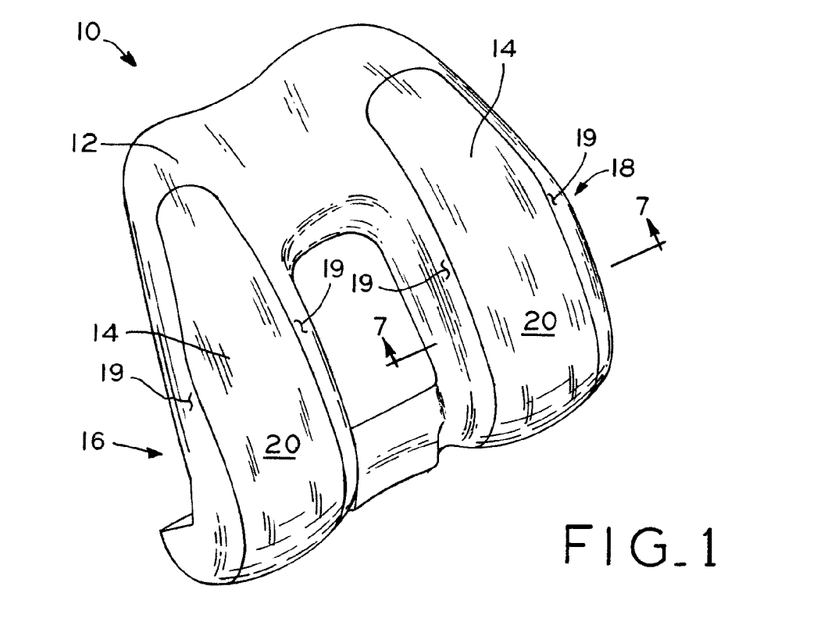
FIG. 1 is a perspective view of an exemplary embodiment of a femoral component of the present invention.
Figure 2:
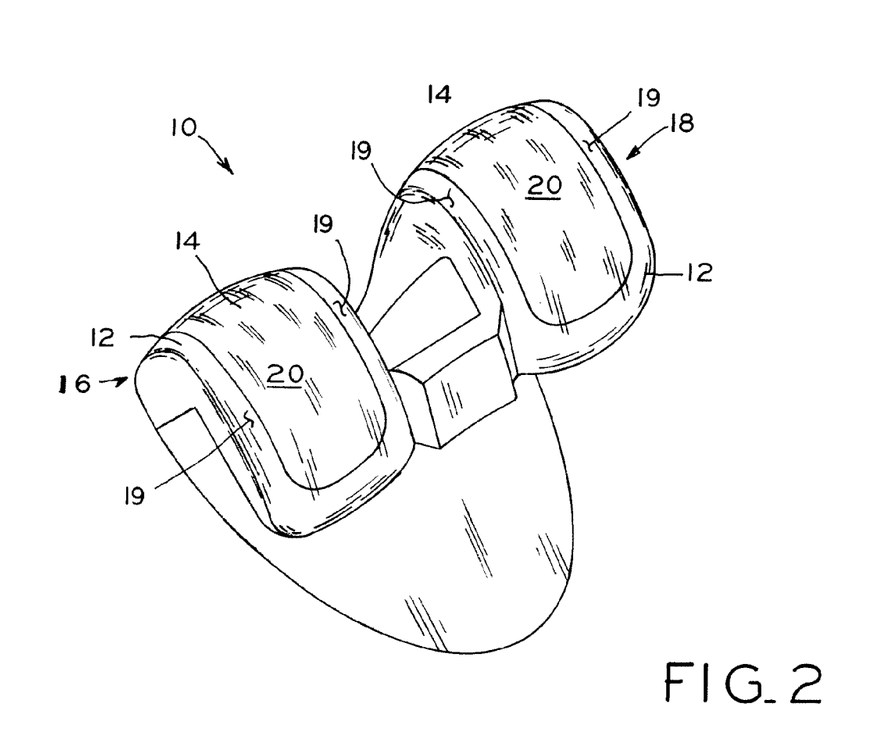
FIG. 2 is another perspective view of the femoral component of FIG. 1.

Referring to FIGS. 1-4, a femoral prosthesis is shown in the form of femoral component 10, which is formed from base material 12 and articulating material 14. Femoral component 10 includes condyle portions 16, 18 that define upper surfaces 19 and are formed from base material 12. As used herein the phrase "condyle portion" is defined as a section of material that has a geometry substantially replicating or mimicking the anatomical geometry of a natural femoral condyle. While several features of femoral prosthesis 10 are described and depicted herein with specific reference to condyle portion 18, condyle portion 16 may be formed in a substantially similar manner and include substantially similar or identical features as condyle portion 18. Additionally, while described and depicted herein as having two condyle portions 16, 18, femoral component 10 may be formed as a unicondylar prosthesis having only a single condyle portion. Referring to FIGS. 1 and 2, articulating material 14 defines articulating surfaces 20 of condyle portions 16, 18.

In one exemplary embodiment, base material 12 and articulating material 14 are selected from different classes of materials. For example, in one exemplary embodiment, base material 12 is a non-polymeric material, such as a biocompatible metal or ceramic, and articulating material 14 is a polymer or hydrogel. For example, if base material 12 is a ceramic, the ceramic may be an oxide ceramic, such as alumina or zirconia; a non-oxide ceramic, such as silicon nitride or silicon carbide; or other ceramic materials that are biologically inert, and yet are sufficiently hard and abrasion resistant. In addition, the ceramic may be a monolith or, alternatively, the ceramic may be a plurality of discrete microscopic or macroscopic particles held in a matrix. Additionally, if base material 12 is a metal, the metal may be titanium, a titanium alloy, cobalt chromium, cobalt chromium molybdenum, stainless steel, porous tantalum, and/or a highly porous biomaterial, for example.

A highly porous biomaterial is useful as a bone substitute and/or a cell and tissue receptive material. A highly porous biomaterial may have a porosity as low as 55, 65, or 75 percent and as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of base material 12 of femoral component 10 to the bone stock of the distal femur.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

As set forth above, in one exemplary embodiment, articulating material 14 of femoral component 10 is a polymer. In this embodiment, articulating material 14 may be polyethylene, a poly ether ether ketone, fiber reinforced poly ether ether ketone, ultrahigh molecular weight polyethylene, crosslinked ultrahigh molecular weight polyethylene, polyether ketone ether ether ketone, poly ether ketone ketone, polycarbonate urethane, polyphenylene, and/or an antioxidant stabilized ultrahigh molecular weight polyethylene, for example. In one exemplary embodiment, articulating material 14 is formed from PrimoSpire™ self reinforced polyphenylene, commercially available for SOLVAY Advanced Polymers, LLC, of Alpharetta, Ga. PrimoSpire™ is a trademark of SOLVAY Advanced Polymers, LLC, of Alpharetta, Ga. Advantageously, by utilizing a rigid base material 12, such as a metal, with a more resilient articulating material 14, such as a polymer, wear of femoral component 10 may be reduced. In another exemplary embodiment, as set forth above, articulating material 14 is a hydrogel. In this embodiment, articulating material 14 may be polyvinyl pyrrolidinone, polyethylene ninyl alcohol, polystyrene allyl alcohol, and/or bisphenos.

Additionally, in one exemplary embodiment, articulating material 14 may be coated with a ceramic layer, which articulates against a tibial component or natural tibia during normal knee articulation. In exemplary embodiments, the ceramic layer on articulating material 14 is formed by methods known by those skilled in the art, such as, by plasma spray, flame spray, HVOF spray, cold spray, or other spray coating technique that provides bonding without substantial degradation of articulating material 14. In addition, the ceramic coating may also be formed on articulating material 14 by ion implantation, ion beam assisted deposition, CVD, or PVD, as is known in the art.

Figure 3:
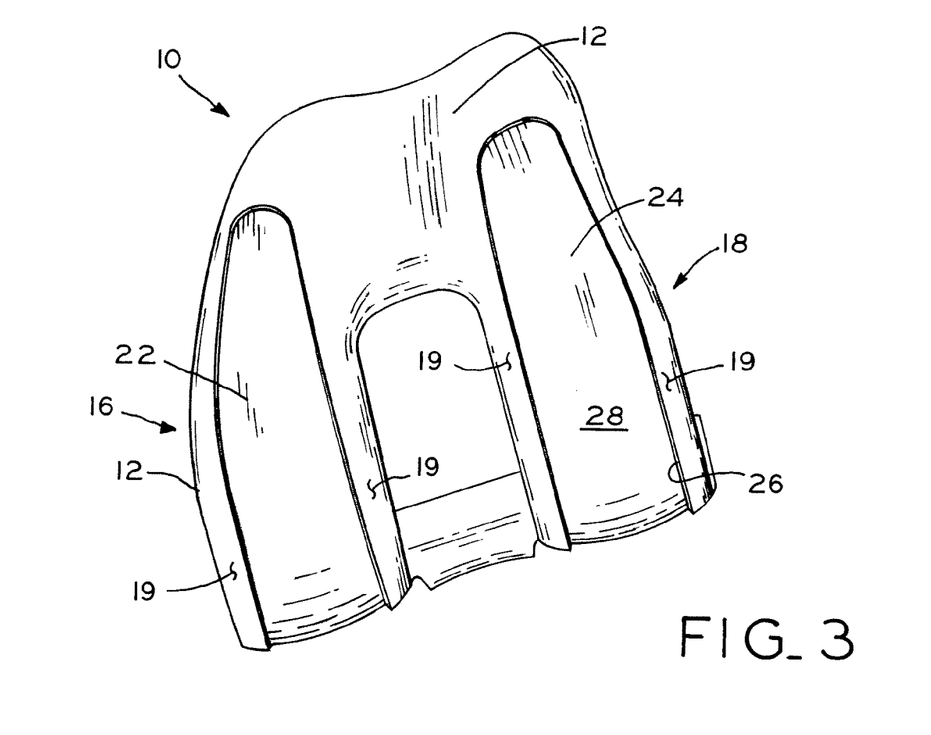
FIG. 3 is a perspective view of the femoral component of FIG. 1 depicting the femoral component prior to the attachment of articulating material.
Figure 4:
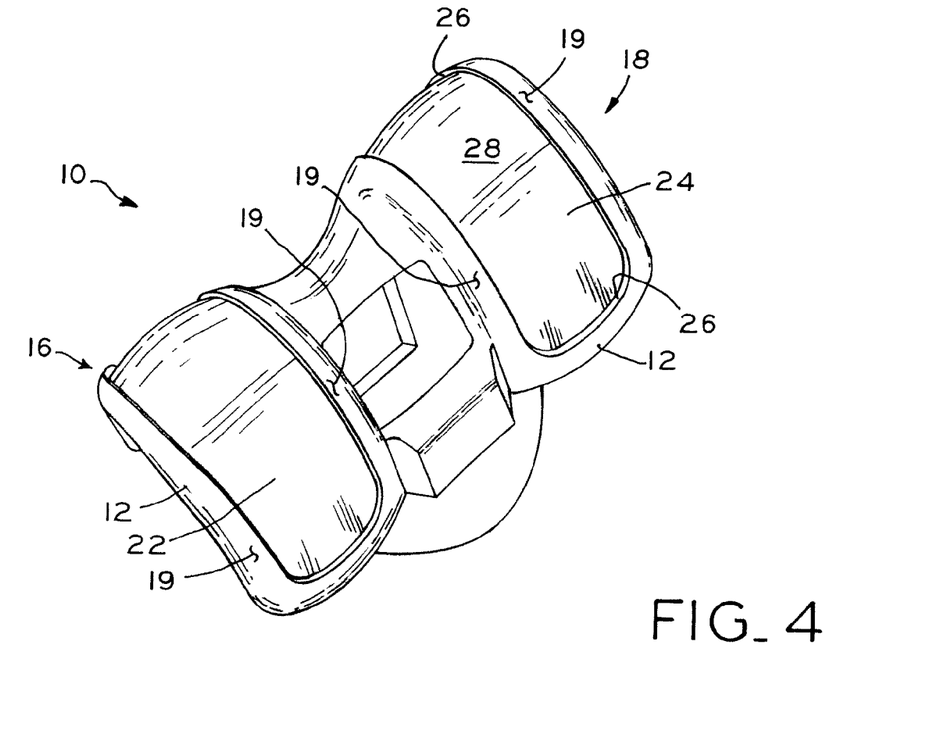
FIG. 4 is another perspective view of the femoral component of FIG. 3.

Referring to FIGS. 3 and 4, grooves 22, 24 are formed within condyle portions 16, 18, respectively, of femoral component 10 for the receipt of articulating material 14. In one exemplary embodiment, grooves 22, 24 are machined into condyle portions 16, 18. In another exemplary embodiment, femoral component 10 is cast and/or formed to include grooves 22, 24. Advantageously, by casting and/or forming femoral component 10 to include grooves 22, 24, the need to machine grooves 22, 24 into femoral component 10 prior to the attachment of articulating material 14 is eliminated. In other exemplary embodiments, grooves 22, 24 may be prepared using a water jet, electrical discharge machining (EDM), and/or grit blasting. Once grooves 22, 24 are properly prepared, articulating material 14 may be received within grooves 22, 24 by the use of an adhesive, welding, thermal spraying, dynamic cold spraying, plasma spraying, insert molding, compression molding, injection molding, laser cladding, and/or press fitting, for example. Additionally, lubricious polymeric materials, such as 2-methacryloyloxy-ethyl phosphorylchlorine can be grafted into groove 22, 24.

Figure 7:
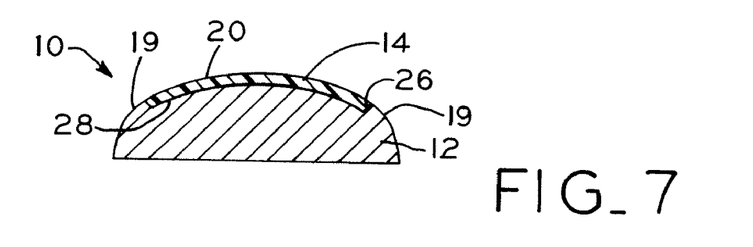
FIG. 7 is a cross-sectional view of the femoral component of FIG. 1 taken along line 7-7 of FIG. 1.

As shown in FIGS. 3 and 4, groove 24 is at least partially defined by wall 26. Wall 26 extends from bottom 28 of groove 24 to upper surface 19 of condyle portion 18. As shown in FIG. 7, articulating material 14 fills groove 24 (FIG. 3) and forms articulating surface 20, which is substantially flush with upper surface 19 of condyle portion 18. Advantageously, by positioning articulating surface 20 substantially flush with upper surface 19, smooth articulation of a tibial prosthesis and/or the natural tibial with femoral component 20 is achieved. Specifically, in the event that during normal knee articulation, a portion of the tibial prosthesis or the natural tibia advances off of articulating surface 20 and onto upper surface 19, this transition will occur smoothly, as no sudden increase and/or decrease in the height of the surface against which the tibial prosthesis or natural tibia is articulating is encountered.

Figure 9:
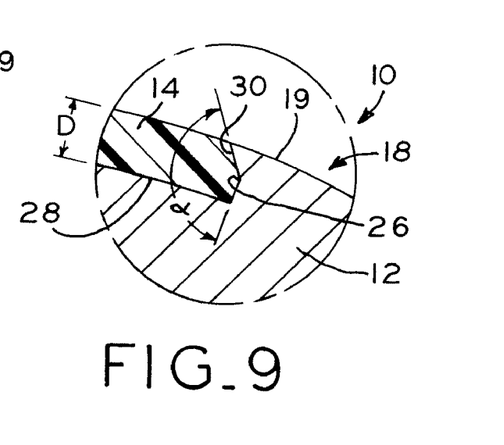
FIG. 9 is an enlarged view of the portion of the femoral component of FIG. 8 encircled in dashed lines.

Referring to FIG. 9, in one exemplary embodiment, depth D of groove 24 is less than or equal to 2 mm. This depth typically provides a sufficient amount of articulating material 14 for articulation against a corresponding tibial component of a knee system or a natural tibia, while allowing base material 12 to provide the additional strength and rigidity needed in condyle portions 16, 18. In other exemplary embodiments, grooves 22, 24 may have a depth D of greater than or less than 2 mm. For example, in exemplary embodiments, grooves 22, 24, may have a depth D as small as 0.5 mm, 1.0 mm, 1.5, mm, or 2.0 mm, and as large as 2.5 mm, 3.0 mm, 3.5 mm, or 4.0 mm. Additionally, while described and depicted herein with specific reference to groove 24, groove 22 of condyle portion 16 may be formed in a substantially similar manner as groove 24.

Advantageously, the design of grooves 22, 24 and the surrounding of articulating material 14 received within grooves 22, 24 by base material 12 substantially prevents the delamination of articulating material 14 from base material 12. Base material 12 of femoral component 10 may be characterized as occupying a volume that is substantially greater than the volume of articulating material 14. Thus, base material 12 and, correspondingly, femoral component 10 may not substantially deflect while under load. The rigidity of base material 12 may permit uniform, predictable, and consistent loading of articulating surface 20. Consequently, when loaded, articulating surface 20 receives substantially uniform frictional contact with an opposing articular surface on the natural tibia or tibial prosthesis, and thus, rigidity of base material 12 may limit abrasion along any specific portion of articulating surface 20. Moreover, articulating material 14 of femoral component 10 may exhibit some elasticity during loading to allow axial deflection or deformation of articulating material 14. Therefore, pressures exerted on femoral component 10 may be partially absorbed during elastic motion of articulating material 14. Further, the additional rigidity provided by base material 12 helps to prevent articulating material 14 from shearing or otherwise separating from base material 12.

Figure 8:
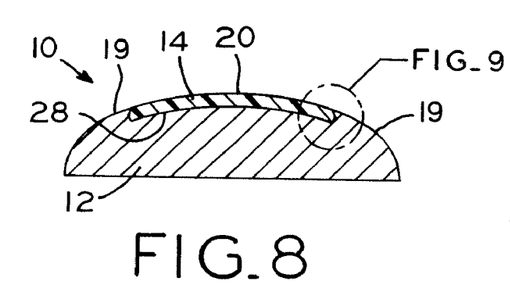
FIG. 8 is a cross-sectional view of another exemplary embodiment of a femoral component of the present invention taken at the same position as the cross-sectional view of FIG. 7.

In another exemplary embodiment, shown in FIGS. 8 and 9, condyle portion 18 further includes lip 30. Lip 30 extends from wall 26 and cooperates with wall 26 to define groove 24. In one exemplary embodiment, shown in FIG. 9, lip 30 extends inwardly from wall 26 in the direction of groove 24 as lip 30 approaches articulating surface 20 and upper surface 19 of condyle portion 18 and forms an obtuse angle α with wall 26. As shown in FIG. 9, angle α extends between wall 26 and lip 30. In exemplary embodiments, angle α is as small as 95 degrees, 120 degrees, 130 degrees, and 145 degrees and as large as 150 degrees, 160 degrees, and 170 degrees.

Further, due to lip 30 extending inwardly from wall 26 in the direction of groove 24, lip 30 facilitates the retention of articulating material 14 within groove 24, as the interaction of lip 30 with articulating material 14 substantially prevents removal and/or delamination of articulating material 14 from groove 24. Specifically, as articulating material 14 advances in the direction of lip 30, articulating material 14 contacts lip 30. In order for a portion of articulating material 14 to be positioned outside of groove 24, at least a portion of articulating material 14 has to be deformed in order to pass by lip 30. However, due to lip 30 extending at least partially over the perimeter of articulating material 14 and the material properties of articulating material 14, articulating material 14 is not deformed during normal knee articulation to the extent necessary to cause articulating material 14 to deform inwardly and allow articulating material 14 to pass by lip 30. Therefore, removal and/or delamination of articulating material 14 from groove 24 is substantially prevented. In addition, attachment of articulating material 14 is improved by base material 12 fully supporting articulating material 14 within groove 24.

Figure 5:
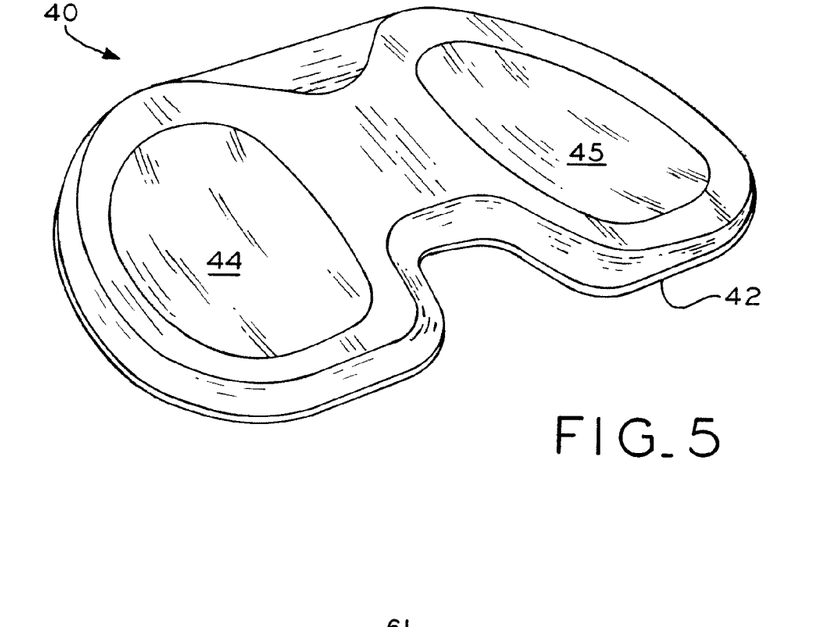
FIG. 5 is a perspective view of an exemplary embodiment of a tibial component of the present invention.

Referring to FIG. 5, a tibial prosthesis is shown in the form of tibial component 40. Tibial component 40 is a monoblock tibial prosthesis, i.e., is formed entirely from a single material, and is configured for independent attachment to the tibia, i.e., is attached to the tibia without the need for using an additional tibial component to support and/or retain tibial component 40 in position. For example, in a traditional tibial prosthesis, the articulating component is supported by and/or secured to a tray component. By using tibial component 40, the need for a tray component is eliminated and tibial component 40 may be secured directly to a tibia in a known manner, such as by a press-fit or with bone cement, for example.

Tibial component 40 includes attachment surface 42 and articulating surfaces 44, 45. Attachment surface 42 is configured for attachment to the bone stock of the proximal end of a tibia. Similarly, articulating surfaces 44, 45 are configured for articulation with articulating surfaces 20 of articulating material 14 of femoral component 10 and/or the condyles of a natural femur. While described and depicted herein as including two articulating surfaces 44, 45 that articulate with opposing natural or prosthetic femoral condyles, tibial component 40 may be formed as a unicondylar prosthesis having only a single articulating surface. In one exemplary embodiment, tibial component 40 is formed from a polymer, such as poly ether ether ketone, fiber reinforced poly ether ether ketone, ultrahigh molecular weight polyethylene, crosslinked ultrahigh molecular weight polyethylene, and polyether ketone ether ether ketone. Alternatively, tibial component 40 may be formed from a hydrogel, such as polyvinyl pyrrolidinone, polyethylene ninyl alcohol, polystyrene allyl alcohol, and bisphenos. In another exemplary embodiment, tibial component 40 is formed from a metal, such as titanium, titanium alloy, cobalt chromium, cobalt chromium molybdenum, porous tantalum, and/or a highly porous biomaterial, for example. Alternatively, in another exemplary embodiment, tibial component 40 is formed from another class of materials, such as ceramics. For example, tibial component 40 may be formed from an oxide ceramic, such as alumina or zirconia; non-oxide ceramic, such as silicon nitride or silicon carbide; or other ceramic materials that are biologically inert, and yet are sufficiently hard and abrasion resistant. In addition, tibial component 40 may be a monolith or, alternatively, may be formed form a plurality of discrete microscopic or macroscopic particles held in a matrix.

Figure 6:
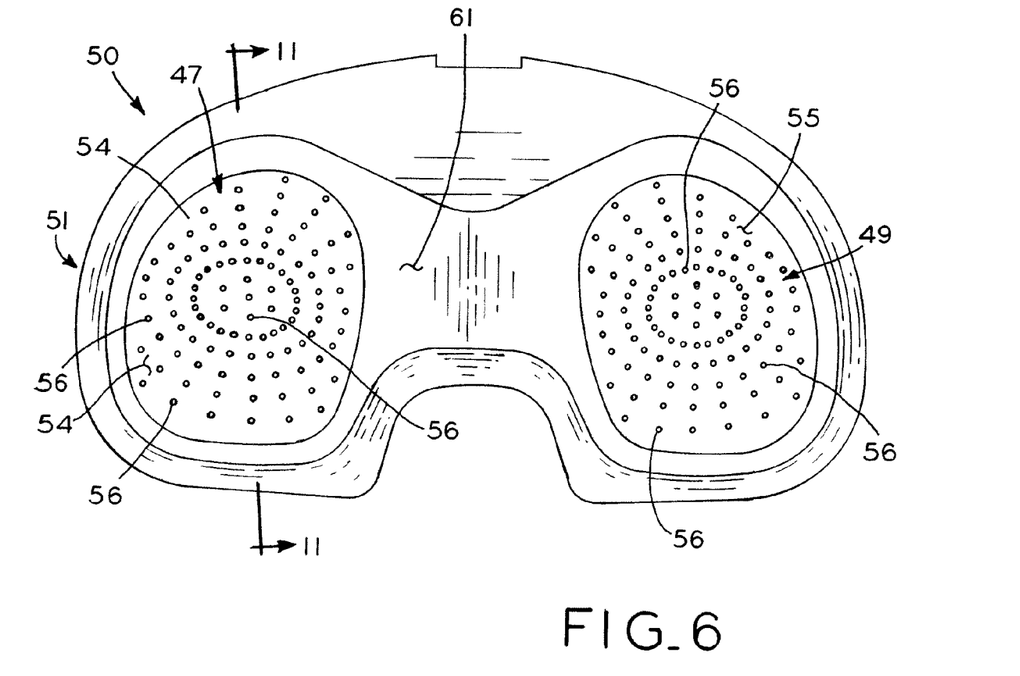
FIG. 6 is a plan view of another exemplary embodiment of a tibial component of the present invention.
Figure 11:
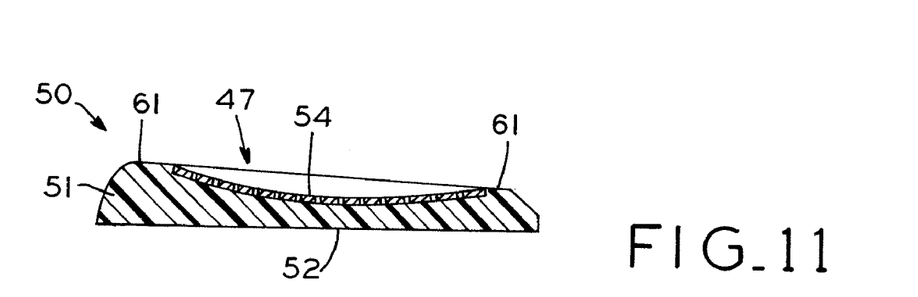
FIG. 11 is a cross-sectional view of the tibial component of FIG. 6, taken along line 11-11 of FIG. 6.

Referring to FIGS. 6 and 11, tibial component 50 is shown including body 51 and articulating portions 47, 49 defining articulating surfaces 54, 55. Body 51 defines upper surface 61 and attachment surface 52 for securement of tibial component 50 to a tibial tray and/or directly to a resected, proximal tibia. As shown in FIG. 11 with respect to articulating portion 47, articulating portions 47, 49 of tibial component 50 are formed independently of body 51 of tibial component 50. Specifically, articulating portions 47, 49 may be formed from a non-polymeric material, such as a biocompatible metal and/or ceramic. For example, if articulating portions 47, 49 are formed from a metal, articulating portions 47, 49 may be formed from titanium, a titanium alloy, cobalt chromium, zirconium alloys, tantalum, and/or cobalt chromium molybdenum. Additionally, if articulating portions 47, 49 are formed from a ceramic, articulating portions 47, 49 may be formed from oxide ceramic, such as alumina or zirconia; non-oxide ceramic, such as silicon nitride or silicon carbide; or other ceramic materials that are biologically inert, and yet are sufficiently hard and abrasion resistant.

In contrast to articulating portions 47, 49, body 51 is formed from a different class of materials, such as polymers, a highly porous biomaterial, or a hydrogel. For example, body 51 may be formed from polyethylene, a poly ether ether ketone, fiber reinforced poly ether ether ketone, ultrahigh molecular weight polyethylene, crosslinked ultrahigh molecular weight polyethylene, polyether ketone ether ether ketone, poly ether ketone ketone, polycarbonate urethane, polyphenylene, PrimoSpire™ self reinforced polyphenylene commercially available from SOLVAY Advanced Polymers, LLC, of Alpharetta, Ga., and/or an antioxidant stabilized ultrahigh molecular weight polyethylene, for example. Additionally, body 51 may be formed from polyvinyl pyrrolidinone, polyethylene ninyl alcohol, polystyrene allyl alcohol, and bisphenos.

Advantageously, by utilizing tibial component 50, body 51, formed, for example, from a polymer, acts to provide cushioning and/or to dampen the shock transmitted to the knee prosthesis during normal joint articulation. Specifically, body 51 of tibial component 50 may exhibit some elasticity during loading to allow axial deflection and/or deformation of the body 51 between the proximal tibia and articulating portions 47, 49. Thus, pressures exerted on tibial component 50 may be partially absorbed and dispersed by body 51 with little or no wear of articulating portions 47, 49. Additionally, in order to reduce friction, the metallic and/or ceramic portions of tibial components 40, 50 may be treated by nitriding or coated with titanium nitride, chromium nitride, molybdenum disulfide, or zirconium nitride. Further, when body 51 is formed from a highly porous biomaterial, a good implant fixation may be achieved.

In order to connect articulating portions 47, 49 to body 51 of tibial component 50, articulating portions 47, 49 may be press-fit into body 51. Alternatively, articulating portions 47, 49 may include a peg or plurality of pegs extending therefrom onto which body 51 may be molded, such as by injection or compression molding, or otherwise formed. Articulating portions 47, 49 may also be secured to body 51 of tibial component 50 with an adhesive, by welding, or by sol gel processing. Regardless of the method used to secure articulating portions 47, 49 to body 51, articulating portions 47, 49 are positioned such that articulating surfaces 54, 55 are flush with upper surface 61 of body 51, as shown in FIG. 11 with respect to articulating surface 54. In this manner, the perimeters of articulating portions 47, 49 are surrounded and supported by body 51. Advantageously, attachment of articulating portions 47, 49 to body 51 is improved by body 51 fully supporting and surrounding articulating portion 47, 49. Further, by positioning articulating surfaces 54, 55 of articulating portions 47, 49 substantially flush with upper surface 61 of body 51, smooth articulation of a femoral prosthesis and/or the natural femur with tibial component 50 is achieved. Specifically, in the event that during normal knee articulation, a portion of the femoral prosthesis or natural femur advances off of either of articulating surfaces 54, 55 and onto upper surface 61, this transition will occur smoothly, as no sudden increase and/or decrease in the height of the surface against which the femoral prosthesis or natural femur is articulating is encountered.

Further, as shown in FIG. 6, articulating surfaces 54, 55 of articulating portions 54, 55 may also include a plurality of dimples 56, such as those disclosed in U.S. patent application Ser. No. 11/684,028, the entire disclosure of which is expressly incorporated by reference herein. Dimples 56 facilitate the retention of synovial fluid and/or other fluids on tibial component 50 to provide lubrication to articulating surfaces 54, 55. To form dimples 56, dimpling, laser ablation, and/or honing may be utilized. Additionally, in one exemplary embodiment, dimples 56 have an RSa roughness of less than 10 micrometers. By having a RSa roughness of less than 10 micrometers, any interference of dimples 56 with the articulation of femoral component 10 and tibial component 50 is substantially eliminated. In order to achieve a RSa roughness of less than 10 micrometers, chemical or electrolytic polishing may be utilized. Additionally, while described and depicted herein with specific reference to articulating surfaces 54, 55 of tibial component 50, dimples 56 may also be applied to articulating surfaces 44, 45 of tibial component 40 and/or articulating surfaces 20 of femoral component 10.

Figure 12:
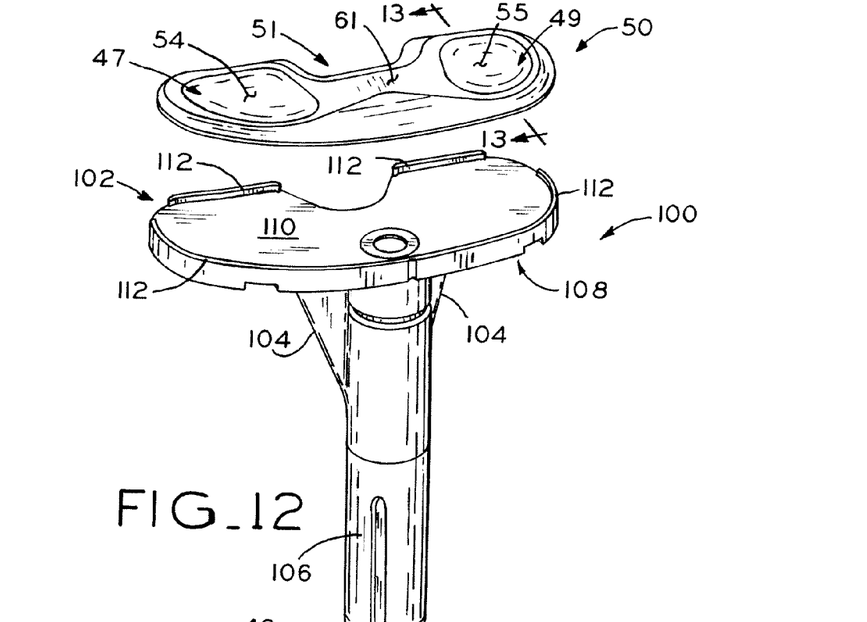
FIG. 12 is an exploded, perspective view of a tibial prosthesis including the tibial component of FIG. 6 and a tibial tray component.
Figure 13:
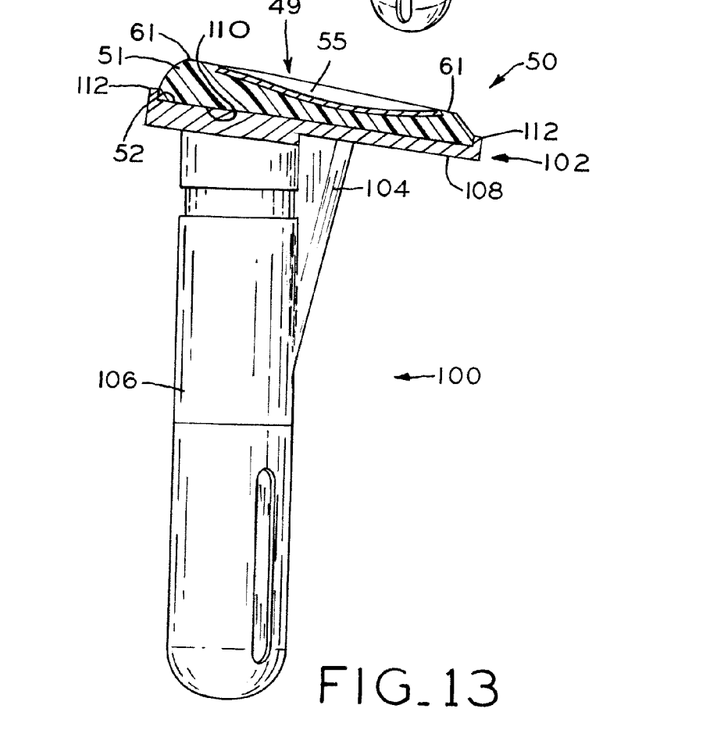
FIG. 13 is a cross-sectional view of the tibial prosthesis of FIG. 12 taken along line 13-13 of FIG. 12.

In one exemplary embodiment, shown in FIGS. 12 and 13, body 51 and, specifically, attachment surface 52 of tibial component 50 are configured to mate with a corresponding tibial tray component 100. Tibial tray component 100 includes plate 102, keel 104, and stem 106. Stem 106 and keel 104 are configured for receipt within the intramedullary canal of the tibia. Keel 104 acts to provide stabilization to tray component 100 and prevent rotation of tray component 100 once tray component 100 has been implanted in the tibia. Plate 102 includes lower surface 108 configured to seat against a resected portion of the proximal tibia. Support surface 110 of plate 102 is configured to receive and support body 51 of tibial component 50 thereon. In one exemplary embodiment, body 51 is secured to plate 102 by forming a snap-fit or an interference fit with plate 102. In one exemplary embodiment, plate 102 includes rim portions 112 extending upwardly from support surface 110. Body 51 of tibial component 50 may be includes recesses that engage rim portions 112 to form a snap-fit or, alternatively, body 51 may be sized such that perimeter surfaces of body 51 form an interference fit with rim portions 112.

In one exemplary embodiment, tray component 100 is formed from a metal. For example, tray component 100 may be formed from titanium, a titanium alloy, cobalt chromium, cobalt chromium molybdenum, stainless steel, porous tantalum, and/or a highly porous biomaterial. Thus, referring to FIG. 13, three different materials may be used to form a tibial prosthesis that supports a femoral component or the natural femur atop a resected proximal tibia during knee articulation. Specifically, a first material may be used to form articulating portions 47, 49 of tibial component 50, a second material may be used to form body 51 of tibial component 50, and a third material may be used to form plate 102 of tray component 100. For example, in one exemplary embodiment, articulating portions 47, 49 may be formed from a ceramic, body 51 of tibial component 50 may be formed from a polymer, and tray component 100 may be formed from a metal. Alternatively, in another exemplary embodiment, articulating portions 47, 49 of tibial component 50 are formed from a first metal, body 51 of tibial component 50 is formed from a polymer, and plate 102 of tray component 100 is formed from a second metal, which is different than the first metal. By adjusting the stiffness of the various components of tibial component 50 and/or tray component 100, a natural knee feel may be achieved.

Figure 10:
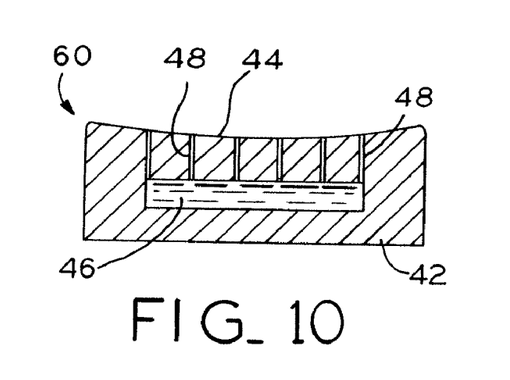
FIG. 10 is a cross-sectional view of another exemplary embodiment of a tibial component of the present invention taken at the same position as the cross-sectional view of FIG. 4.

Another exemplary embodiment of tibial component 40 is shown in FIG. 10 as tibial component 60. Tibial component 60 is substantially similar to tibial component 40 and corresponding reference numerals have been used to identify identical or substantially identical features therebetween. Tibial component 60 further includes chamber 46 formed therein. Specifically, chamber 46 is formed within tibial component 60 between attachment surface 42 and articulating surface 44. Chamber 46 may have a length of up to substantially 10 mm and a height of up to substantially 3 mm. As a result of forming tibial component 60 as a monoblock or monolith, sufficient rigidity and strength is provided by tibial component 60 even after chamber 46 is formed therein. Passageways 48, which in one exemplary embodiment are microsized, extend from chamber 46 to articulating surface 44 of tibial component 60. In this embodiment, fluid, such as an antibiotic, medicinal, synovial, and/or other fluids, may be received within chamber 46. Then, during natural articulation of tibial component 60 with femoral component 10, the fluid contained within chamber 46 may travel through passageways 48 and exit to articulating surfaced 44. Thus, by utilizing chamber 46 and passageways 48 in conjunction with tibial component 60, a mechanism for providing continual lubrication or medicinal treatment to the knee joint is provided.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A knee prosthesis, comprising:
  a femoral component formed from a non-polymeric base material and a polymer articulating material, said femoral component having at least one condyle portion formed from said non-polymeric base material, said at least one condyle portion having an upper surface, a wall at least partially defining a groove, and a lip extending from said wall into said groove, said lip and said wall of said at least one condyle portion defining an obtuse angle, said polymer articulating material received within said groove, said wall and said lip of said at least one condyle portion surrounding said polymer articulating material, wherein said lip facilitates retention of said polymer articulating material within said groove, said polymer articulating material defining an articulation surface configured for articulation against one of a proximal tibial prosthesis and a natural proximal tibia, said articulation surface of said polymer articulating material positioned substantially flush with said upper surface of said at least one condyle portion.

2. The knee prosthesis of claim 1, wherein said non-polymeric base material comprises a metal.

3. The knee prosthesis of claim 2, wherein said non-polymeric base material is selected from the group consisting of titanium, a titanium alloy, cobalt chromium, cobalt chromium molybdenum, stainless steel, and porous tantalum.

4. The knee prosthesis of claim 1, wherein said non-polymeric base material comprises a ceramic.

5. The knee prosthesis of claim 4, wherein said non-polymeric base material is selected from the group consisting of alumina, zirconia, silicon nitride, and silicon carbide.

6. The knee prosthesis of claim 1, wherein said polymer articulating material is selected from the group consisting of poly ether ether ketone, fiber reinforced poly ether ether ketone, ultra high molecular weight polyethylene, cross-linked ultra high molecular weight polyethylene, polycarbonate urethane, polyphenylene, and polyether ketone ether ether ketone.

7. The knee prosthesis of claim 1, wherein said articulating material is positioned in said groove by one of thermal spraying, dynamic cold spraying, insert molding, compression molding, injection molding, laser cladding, and press fitting.

* * * * *